United States Patent [19]

Disteldorf et al.

[11] Patent Number: 4,526,971
[45] Date of Patent: Jul. 2, 1985

[54] PROCESS FOR THE PRODUCTION OF POLYALKYLPIPERIDYLAMINES

[75] Inventors: Josef Disteldorf, Herne; Manfred zur Hausen, Marl; Werner Hübel; Gunter Kriebel, both of Herne, all of Fed. Rep. of Germany

[73] Assignee: Chemische Werke Huls Aktiengesellschaft, Marl, Fed. Rep. of Germany

[21] Appl. No.: 595,555

[22] Filed: Mar. 30, 1984

[30] Foreign Application Priority Data

Jun. 13, 1983 [DE] Fed. Rep. of Germany ....... 3321332

[51] Int. Cl.³ ................ C07D 401/12; C07D 211/58
[52] U.S. Cl. .................................... 546/186; 546/191
[58] Field of Search ............................... 546/191, 186

[56] References Cited
U.S. PATENT DOCUMENTS
4,415,688 11/1983 Minagawa et al. ................. 546/186

Primary Examiner—Paul R. Michl
Assistant Examiner—Alex H. Walker
Attorney, Agent, or Firm—Oblon, Fisher, Spivak, McClelland & Maier

[57] ABSTRACT

A process for producing polyalkylpiperidylamines of the formula (I):

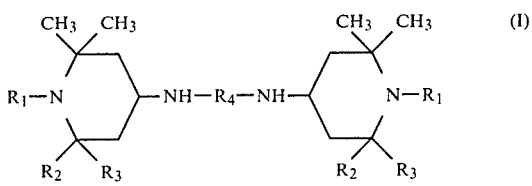

wherein $R_1$ is hydrogen or a $C_1$–$C_{12}$ alkylradical; $R_2$ and $R_3$ are each $C_1$–$C_5$ alkylradicals or $R_2$ and $R_3$, taken together, are —(CH)—$_a$ or —CH$_2$—NR$_1$—C(R$_5$,R$_6$)—CH$_2$—; $R_4$ is a $C_2$–$C_{18}$ alkylene radical, which is unsubstituted or substituted by $C_1$–$C_3$ alkyl; a $C_5$–$C_{12}$ cycloalkylene radical, which is unsubstituted or is methyl-substituted; a cycloalkylene radical of the formula

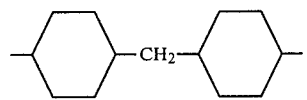

where the cyclohexyl rings are unsubstituted or are methyl-substituted; or groups of the formula —(CH$_2$)$_k$—X—[CH$_2$)$_m$—X]—$_n$(CH$_2$)$_p$—, where X is —O—, —NH—, —NR$_5$ and R$_5$ and R$_6$ are each a $C_1$–$C_5$ alkyl radical and a is 4 or 5, k is 2 or 3, n is 0-3 and p is 2 or 3; which process involves reductively alkylating an alkylated 4-aminopiperidine of the formula (II):

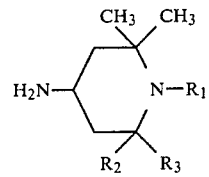

with a difunctional alcohol of the formula HO—R$_4$—OH, wherein $R_1$ and $R_4$ have the above definitions.

13 Claims, No Drawings

PROCESS FOR THE PRODUCTION OF POLYALKYLPIPERIDYLAMINES

BACKGROUND OF THE INVENTION

1. Field of the Invention:

The present invention relates to a process for the production of polyalkylpiperidylamines.

2. Description of the Prior Art:

Polyalkylpiperidylamines should properly be called dimers due to the number of piperidine units they contain. They are distinguished from piperidylamines, which contain only one piperidine unit (monomer) or more than four piperidine units (polymer). Polyalkylpiperidylamines are valuable intermediates, especially for the synthesis of plastic additives.

Currently, polyalkylpiperidylamines are prepared by the reductive amination of polyalkyl-4-piperidones. For example, the process of GB-PS No. 834 290 involves the reaction of 2,2,6,6-tetramethyl-4-piperidone with dialkylaminoalkylamines in the presence of a platinum-/activated carbon catalyst and hydrogen to form 2,2,6,6-tetramethylpiperidine substituted at the 4-position.

DE-OS No. 23 49 962 describes the reductive amination of 1-benzyl-2,2,6,6-tetramethyl-4-piperidone with butylamine in methyl alcohol on a platinum catalyst.

In another example of a reductive amination technique, DE-OS No. 26 11 208 discloses the reductive amination of 2,2,6,6-tetraalkyl-4-piperidone with alkylenediamines on platinum catalysts and the subsequent reaction of the resulting dimer polyalkylpiperidylamines with difunctional compounds, which contain halogen and/or epoxy groups, to form polymeric polyalkylpiperidylamines.

DE-OS No. 26 21 870 describes the reductive amination of 2,2,6,6-tetramethyl-4-piperidone in the presence of a Raney nickel catalyst.

Additionally, DE-OS No. 30 07 996 discloses reductive amination of 2,2,6,6-tetramethyl-4-piperidone with mono- or di-amines on cobalt and nickel catalysts. It is also recommended that the reaction water formed during condensation be removed by azeotropic distillation before commencing hydrogenation.

All of the above-described processes suffer from at least one serious disadvantage. For example, in the first three processes described above, the use of expensive noble metal catalysts is disadvantageous, as these catalysts cannot be regenerated without loss. Raney catalysts, which are used in the fourth process described above, are essentially best suited for batch processes. Reuse of the catalysts is complicated and use in a continuous process requires considerable expense.

Moreover, as the last described process illustrates, it is advantageous in the reductive amination of 2,2,6,6-tetramethyl-4-piperidone that the reaction water be removed from the reaction mixture as quickly as possible. The reason for this is the ease with which 2,2,6,6-tetramethyl-4-piperidone is hydrolyzed, particularly at higher temperatures. This tendency has lead to yield losses.

An alternative approach to the production of polyalkylpiperidylamines is set forth in DE-OS No. 26 11 208. This approach entails the reaction of 4-aminopolyalkyl-piperidines with dihalide compounds in the presence of alkali compounds to neutralize the nascent hydrogen halides. Although high polyalkylpiperidylamine yields are attained, the use of alkali compounds and the accumulation of considerable amounts of salts are a considerable disadvantage. Also, because of the high water solubility of polyalkylpiperidylamines, considerable product losses occur in separation from the reaction mixture.

Finally, the present inventors attempted to produce dimer polyalkylpiperidylamines by the hydrogenating alkylation of diamines with polyalkylpiperidimes hydroxylated in the 4-position and found the results to be unsatisfactory. It was found that under the reaction conditions, the diamines react with one another. For example, when ethylenediamine was used, piperazine was obtained, and when hexamethylenediamine was used, azacycloheptane was obtained. Thus, a breakthrough with the process of hydrogenating alkylation of amines, as described in Houben-Weyl, Vol. XI/1, P. 126 ff, appears most unlikely.

Therefore, a need clearly continues to exist for a process for the production of polyalkylpiperidylamines which produces satisfactory yields of the product, and which does not entail the use of expensive noble metal catalysts, Raney catalysts or alkali compounds.

SUMMARY OF THE INVENTION

Accordingly, it is an object of the present invention to provide a process for the production of polyalkylpiperidylamines which produces these compounds in satisfactory yield without using expensive noble metal catalysts, Raney catalysts or alkali compounds.

It is also an object of this invention to provide a process for the production of polyalkylpiperidylamines whereby considerable losses of the product, due to separation of the product from the reaction mixture into water, do not occur.

According to the present invention, the foregoing and other objects are attained by providing a process for producing polyalkylpiperidylamines of the formula (I):

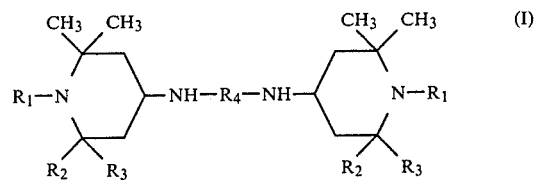

wherein $R_1$ is hydrogen or a $C_1$–$C_{12}$ alkyl radical; $R_2$ and $R_3$ are each $C_1$–$C_5$ alkyl radicals or $R_2$ and $R_3$, taken together, are $-(CH_2)-_a$ or $-CH_2-C(CH_3)_2-NR_1-C(R_5,R_6)-CH_2-$; $R_4$ is a $C_2$–$C_{18}$ alkylene radical which is unsubstituted or substituted by $C_1$–$C_3$ alkyl; a $C_5$–$C_{12}$ cycloalkylene radical, which is unsubstituted or is methyl-substituted; a cycloalkylene radical of the formula

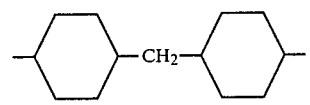

where the cyclohexyl rings are unsubstituted or are methyl-substituted; or groups of the formula: $-(CH_2)_k-X-[(CH_2)_m-X]_n-(CH_2)_p-$, where X is $-O-$, $-NH-$ or $-NR_5-$ and $R_5$ and $R_6$ are each a $C_1$–$C_5$ alkyl radical and a is 4 or 5, k is 2 or 3, m is 2 or 3, n is 0–3 and p is 2 or 3; which process involves reductively alkylating an alkylated 4-aminopiperidine of the formula (II):

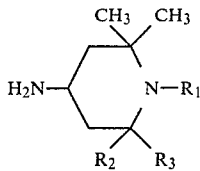

with a difunctional alcohol of the formula HO—R$_4$—OH, wherein R$_1$, R$_2$, R$_3$ and R$_4$ have the above definitions.

DETAILED DESCRIPTION OF THE PREFERRED EMBODIMENTS

According to the present invention a process is now provided for the production of dimer polyalkylpiperidylamines, starting from 4-aminopiperidines of the formula (II):

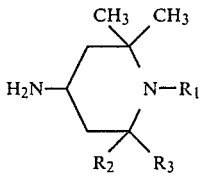

wherein R$_1$ is hydrogen or a C$_1$-C$_{12}$ alkyl radical. Suprisingly, it has been found that the desired dimer polyalkylpiperidylamines are obtained by reductive alkylation of alkylated 4-aminopiperidines with difunctional alcohols. The process of the present invention is performed in accordance with the following reaction scheme:

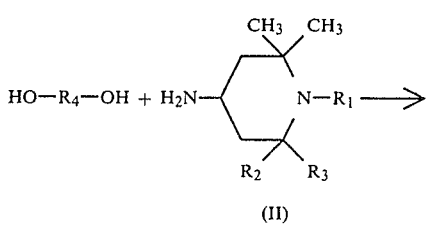

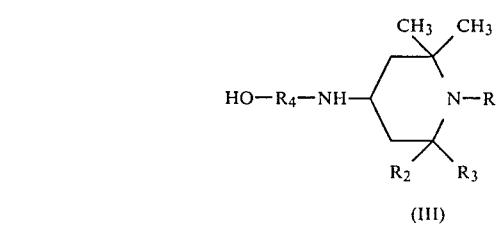

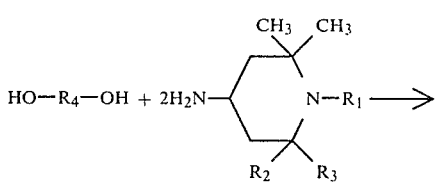

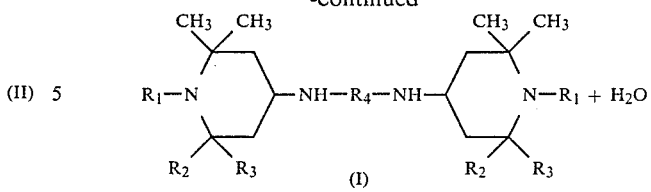

Various mixtures of compounds I and III are obtained, depending on the molar ratio at which the reaction is performed. The reaction can be so directed by recycling III that only I results.

The reaction

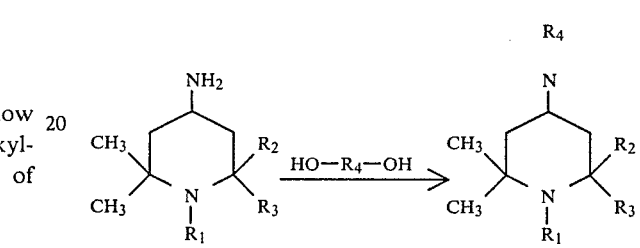

whose extent depends both on the dialcohol component and the reaction conditions, is observed as a secondary reaction. Formation of bis(2,2,6,6-tetramethyl-4-piperidyl)amine

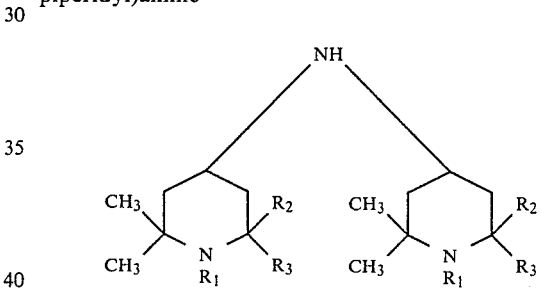

is observed to a very limited extent.

The 4-aminopolyalkylpiperidines (II) are preferably used in excess relative to the diol component.

The reaction temperatures are about 120° to 250° C., especially about 160° to 220° C., preferably about 180° to 200° C. Coper chromite catalysts, which preferably are activated by addition of barium oxide, are suitable catalysts. The catalyst throughput, in the preferred continuous operation with the trickle process, amounts to about 0.1 to 3 VHSV, relative to the mixture used. VHSVs of about 0.2 to 1, especially about 0.2 to 0.5, are particularly advantageous.

The required hydrogen pressure is between about 1 and 300 bars, preferably the pressure range will be from about 3 to 30 bars.

4-Amino-2,2,6,6-tetramethylpiperidine is preferred as the 4-aminopolyalkylpiperdine.

Suitable dialcohol components are, e.g., ethylene glycol, diethylene glycol, triethylene glycol, 1,3-propanediol, 3,7-dioxa-1,5-nonanediol, diethanolamine, bishydroxyethylemethylamine, 1,4-butanediol, 1,6-hexanediol, 1,12-dodecanediol, 2,2,4-trimethyl-1,6-hexanediol, 2,4,4-trimethyl-1,6-hexanediol, 1,4-cyclohexanediol, 4,4'-dihydroxycyclohexylmethane, N,N'-bis-2-hydroxyethylpiperazine. 1,6-hexanediol is preferred.

The present invention will be further illustrated by certain examples and references which are provided for purposes of illustration only and are not intended to limit the presention invention.

EXAMPLE

N,N'-bis(2,2,6,6-tetramethyl-4-piperidyl)hexamethylenediamine

A mixture of 4-amino-2,2,6,6-tetramethylpiperidine and 1,6-hexanediol in a molar ratio of 4:1 is reacted in a 1-liter shaft oven which is filled with 500 ml of reduced copper chromite catalyst (Harshaw Cu 1107 of Harshaw Chemical Co, DE-5632 Wermelskirchen) at 180° C. and 30 bars of hydrogen hourly.

According to GC analysis, the initial product after a 10 day test period, contains 73.1% 4-amino-2,2,6,6-tetramethylpiperidine
9.8% 1,6-hexanediol
1.0% 4-hexamethyleneimino-2,2,6,6-tetramethylpiperidine
0.55% bis(2,2,6,6-tetramethyl-4-piperidyl)amine
6.5% 4-(6-hydroxyhexylamino)piperidine
9.0% N,N'-bis(2,2,6,6-tetramethyl-4-piperidyl)hexamethylenediamine This corresponds to a 14.4% conversion to 4-amino-2,2,6,6-tetramethylpiperidine and a 38.7 conversion to 1,6-hexanediol and, considering the ability of the 4-amino-2,2,6,6-tetramethylpiperidine, 1,6-hexanediol and 4-(6-hydroxylhexylamino)-2,2,6,6-tetramethylpiperidine to be recycled, it corresponds to a yield of N,N'-bis(2,2,6,6-tetramethyl-4-piperidyl)hexamethylenediamine of 89.9%, relative to 4-amino-2,2,6,6-tetramethylpiperidine, and 92.0%, relative to 1,6-hexanediol.

By further distillative processing there were isolated:
4-hexamethyleneimino-2,2,6,6-tetramethylpiperidine
  $bp_{10} = 150°$ C., $n_D{}^{25} = 1.4870$
bis(2,2,6,6-tetramethyl-4-piperidyl)amine
  $bp_{14} = 180°$ C., mp=74°-77° C.
4-(6-hydroxyhexylamino)-2,2,6,6-tetramethylpiperidine
  $bp_{27} = 195°$ C., mp=80°-81° C.
N,N'-bis(2,2,6,6-tetramethyl-4-piperidyl)hexamethylenediamine
  $bp_{28} = 253°$ C., mp=60.5°-61.5° C.

The pressure values of the boiling points were given in torrs.

No decline in the activity of the catalyst was observed after a 60-day test period.

Having now fully described this invention, it will be apparent to one of ordinary skill in the art that many changes and modifications can be made thereto without departing from the spirit or scope of the invention as set forth herein.

What is claimed as new and intended to be secured by Letters Patent is:

1. A process for producing polyalkylpiperidylamines of the formula (I):

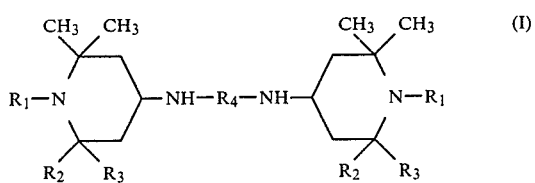

wherein $R_1$ is hydrogen or a $C_1$-$C_{12}$ alkyl radical; $R_2$ and $R_3$ are each $C_1$-$C_5$ alkyl radicals or $R_2$ and $R_3$, taken together are —$(CH_2)_a$— or —$CH_2$—$C(CH_3)_2$—$NR_1$—$C(R_5,R_6)$—$CH_2$—; $R_4$ is a $C_2$-$C_{18}$ alkylene radical, which is unsubstituted or substituted by $C_1$-$C_3$ alkyl; a $C_5$-$C_{12}$ cycloalkylene radical, which is unsubstituted or is methyl-substituted; a cycloalkylene radical of the formula

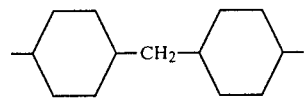

where the cyclohexyl rings are unsubstituted or are methyl-substituted; or groups of the formula —$(CH_2)_k$—$X$—$[(CH_2)_m$—$X]_n$—$(CH_2)_p$, where X is —O—, —NH—, —$NR_5$— and $R_5$ and $R_6$ are each a $C_1$-$C_5$ alkyl radical and a is 4 or 5, k is 2 or 3, m is 2 or 3, n is 0-3 and p is 2 or 3; which process comprises reductively alkylating an alkylated 4-aminopiperidine of the formula (II);

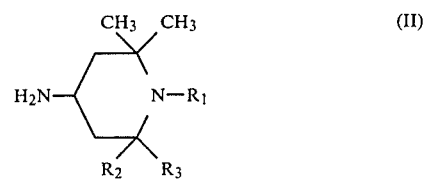

with a difunctional alcohol of the formula HO—$R_4$—OH, wherein $R_1$, $R_2$, $R_3$ and $R_4$ have the above definitions.

2. The process as in claim 1, wherein the reaction is conducted at a hydrogen pressure of about 1 to 300 bars in the presence of a copper chromite catalyst.

3. The process as in claim 2, wherein said hydrogen pressure is about 3 to 30 bars.

4. The process as in claim 2, wherein said copper chromite catalyst is activated by the addition of barium oxide prior to use.

5. The process as in claim 1, wherein said alkylated 4-aminopiperidine is reacted with said dialcohol in a molar ratio of about 10:1.

6. The process as in claim 5, wherein the molar ratio of said alkylated 4-aminopiperidine to said dialcohol is in the range of 4:1 to 2:1.

7. The process as in claim 1, wherein the reaction is conducted at a temperature in the range of 120° to 250° C.

8. The process as in claim 7, wherein said reaction temperature is in the range of 180° to 200° C.

9. The process as in claim 1, wherein the VHSV of the mixture used of the alkylated 4-aminopiperidine and difunctional alcohol has a VHSV of about 0.1 to 3.

10. The process as in claim 9, wherein said VHSV of the mixture is about 0.2 to 0.5.

11. The process as in claim 1, wherein 4-amino-2,2,6,6-tetramethylpiperidine is used as said alkylated 4-aminopiperidine.

12. The process as in claim 1, wherein said difunctional alcohol is selected from the group consisting of ethylene glycol, diethylene glycol, triethylene glycol, 1,3-propanediol, 3,7-dioxa-1,5-nonanediol, diethanolamine, bis-hydroxethylmethylamine, 1,4-butanediol, 1,6-hexanediol, 1,12-dodecanediol, 2,2,4-trimethyl-1,6-hexanediol, 2,4,4-trimethyl-1,6-hexanediol, 1,4-cyclohexanediol, 4,4'-dihydroxycyclohexylmethane, N,N'-bis-2-hydroyethyl piperazine.

13. The process as in claim 12, wherein said difunctional alcohol is 1,6-hexanediol.

* * * * *